US006243131B1

(12) United States Patent
Martin

(10) Patent No.: US 6,243,131 B1
(45) Date of Patent: *Jun. 5, 2001

(54) METHOD FOR DIRECTLY SCANNING A RECTILINEAR IMAGING ELEMENT USING A NON-LINEAR SCAN

(75) Inventor: H. Lee Martin, Knoxville, TN (US)

(73) Assignee: Interactive Pictures Corporation, Knoxville, TN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/373,446

(22) Filed: Jan. 17, 1995

Related U.S. Application Data

(63) Continuation-in-part of application No. 08/189,585, filed on Jan. 31, 1994, now Pat. No. 5,384,588, which is a continuation-in-part of application No. 08/014,508, filed on Feb. 8, 1993, now Pat. No. 5,359,363, which is a continuation-in-part of application No. 07/699,366, filed on May 13, 1991, now Pat. No. 5,185,667.

(51) Int. Cl.[7] .............................. H04N 7/00; H04N 5/225
(52) U.S. Cl. .......................... 348/36; 348/207; 348/206; 348/147; 348/335; 382/293
(58) Field of Search ................................. 348/36, 43, 44, 348/39, 46, 147, 143, 315, 335, 340, 294, 311, 342, 91; 382/293, 295, 296, 297, 298; 395/137–139; 257/231; H04N 5/30, 7/00, 5/225, 1/18

(56) References Cited

U.S. PATENT DOCUMENTS 3,234,394   2/1966   Worden .
3,723,805   3/1973   Scarpino et al. ................ 315/27 GD
4,125,862   11/1978  Catano ................................. 358/140
4,152,724   5/1979   Hunter ................................. 358/109

(List continued on next page.)

FOREIGN PATENT DOCUMENTS 2-127877      5/1990   (JP) .............................. H04N/5/225
WO 82/03712  10/1982   (WO) ............................ H04N/5/225

OTHER PUBLICATIONS

English Abstract 2–127877 (A), May 16, 1990, for "Electronic Still Camera Provided With Fisheye Lens" for Japanese Application No. 63–281550.

(List continued on next page.)

Primary Examiner—Michael H. Lee
(74) Attorney, Agent, or Firm—Banner & Witcoff, Ltd.

(57) ABSTRACT

A method for capturing and directly scanning a rectilinear imaging element using a non-linear scan is incorporated into a single chip comprising at least a sensor array and an MSD. The method directly addresses each picture element of an analog image captured with an imaging device having either a partial spherical field of view or a conventional two-dimensional field of view. An image transform processor is used to process the captured image depending upon the particular portion of interest of the image. In the case of a non-linear scan, the image transform processor is provided with the capability of geometrically filtering the portion of interest of the captured image such that a two-dimensional, undistorted image is displayed at the monitor. A CMOS active pixel image sensor (APS) or Charge Injection Diode (CID) camera array are used to capture the image to be scanned. The image transform processor of the present invention is a Mixed-signal Semiconductor Device (MSD). The image transform processor corrects any predetermined distortion introduced by the image sensor array.

17 Claims, 9 Drawing Sheets

U.S. PATENT DOCUMENTS

| | | | |
|---|---|---|---|
| 4,191,967 | 3/1980 | Dansac et al. | 358/113 |
| 4,204,230 | 5/1980 | Sprague . | |
| 4,240,727 | 12/1980 | Lermann et al. . | |
| 4,463,380 | 7/1984 | Hooks, Jr. | 358/160 |
| 4,518,898 | 5/1985 | Tarnowski et al. | 315/371 |
| 4,549,208 | 10/1985 | Kamejima et al. | 358/108 |
| 4,554,585 | 11/1985 | Carlson . | |
| 4,574,311 | 3/1986 | Resnikoff et al. . | |
| 4,602,289 | 7/1986 | Sekine . | |
| 4,661,855 | 4/1987 | Gülck | 358/225 |
| 4,670,648 | 6/1987 | Hall et al. | 250/216 |
| 4,683,498 | 7/1987 | Topper . | |
| 4,720,746 | 1/1988 | Moore . | |
| 4,728,839 | 3/1988 | Coughlan et al. | 310/112 |
| 4,736,436 | 4/1988 | Yasukawa et al. . | |
| 4,740,839 | 4/1988 | Phillips . | |
| 4,751,660 | 6/1988 | Hedley | 364/518 |
| 4,752,831 | 6/1988 | Biber et al. . | |
| 4,757,384 | 7/1988 | Nonweiler et al. . | |
| 4,772,942 | 9/1988 | Tuck | 358/87 |
| 4,797,562 | 1/1989 | Dietrich . | |
| 4,797,942 | 1/1989 | Burt | 382/41 |
| 4,807,158 | 2/1989 | Blanton et al. . | |
| 4,819,070 | 4/1989 | Hynecek . | |
| 4,835,532 | 5/1989 | Fant | 340/728 |
| 4,837,429 | 6/1989 | Umezawa et al. . | |
| 4,843,475 | 6/1989 | Imai . | |
| 4,858,002 | 8/1989 | Zobel | 358/98 |
| 4,858,014 * | 8/1989 | Zeevi et al. | 348/206 |
| 4,858,149 | 8/1989 | Quarendon | 364/522 |
| 4,877,959 | 10/1989 | Page . | |
| 4,882,478 | 11/1989 | Hayashi et al. . | |
| 4,893,025 | 1/1990 | Lee . | |
| 4,899,293 | 2/1990 | Dawson et al. . | |
| 4,918,473 | 4/1990 | Blackshear | 354/81 |
| 4,924,094 | 5/1990 | Moore | 250/334 |
| 4,928,174 | 5/1990 | Smith . | |
| 4,942,473 * | 7/1990 | Zeevi et al. | 348/281 |
| 4,945,367 | 7/1990 | Blackshear | 354/81 |
| 4,965,844 | 10/1990 | Oka et al. | 382/44 |
| 4,991,020 | 2/1991 | Zwirn | 358/160 |
| 5,005,083 | 4/1991 | Grage et al. | 358/181 |
| 5,019,912 | 5/1991 | Matsuda . | |
| 5,020,114 | 5/1991 | Fujioka et al. | 382/44 |
| 5,023,725 | 6/1991 | McCutchen | 358/231 |
| 5,043,817 | 8/1991 | Kinugasa et al. . | |
| 5,048,102 | 9/1991 | Tararine et al. | 382/41 |
| 5,057,923 | 10/1991 | Matsuda . | |
| 5,067,019 | 11/1991 | Juday et al. | 358/160 |
| 5,068,735 | 11/1991 | Tuchiya et al. | 358/209 |
| 5,077,609 | 12/1991 | Manelphe | 358/109 |
| 5,107,122 | 4/1992 | Barkan et al. . | |
| 5,140,395 | 8/1992 | Beland et al. . | |
| 5,173,948 | 12/1992 | Blackham et al. | 382/44 |
| 5,175,808 | 12/1992 | Sayre . | |
| 5,185,667 | 2/1993 | Zimmermann | 358/209 |
| 5,200,818 | 4/1993 | Neta et al. | 358/87 |
| 5,231,673 | 7/1993 | Elenga | 382/6 |
| 5,243,433 | 9/1993 | Hailey . | |
| 5,276,519 | 1/1994 | Richards et al. . | |
| 5,276,521 | 1/1994 | Mori . | |
| 5,313,306 | 5/1994 | Kuban et al. . | |
| 5,359,363 | 10/1994 | Kuban et al. . | |
| 5,396,583 | 3/1995 | Chen et al. . | |
| 5,428,390 | 6/1995 | Cooper et al. . | |
| 5,489,940 | 2/1996 | Richardson et al. | 348/315 |
| 5,905,530 * | 5/1999 | Yokota et al. | 348/240 |

OTHER PUBLICATIONS

"Fooling the Eye", Suzanne Oliver, Forbes, Jan. 16, 1995 (page 94).

Exhibit 4 –"The Omnigraph, Omnidirectional Spherical Photography" and "Omnigraphics, second report," Richard J. Felix, 1979's.

Exhibits 6, 26, 29, 30, 32–35 —Omnigraphics course materials, California State University —Richard J. Felix —1974 to 1994.

Exhibit 17 —"Multiplex Video Display", Richard J. Felix, Feb. 7, 1994.

* cited by examiner

METHOD FOR DIRECTLY SCANNING A RECTILINEAR IMAGING ELEMENT USING A NON-LINEAR SCAN

This application is a continuation-in-part of U.S. application Ser. No. 08/189,585 filed Jan. 31, 1994, now U.S. Pat. No. 5,384,588, which is a continuation-in-part of U.S. application Ser. No. 08/014,508 filed Feb. 8, 1993, now U.S. Pat. No. 5,359,363, which is a continuation-in-part of U.S. application Ser. No. 07/699,366 filed May 13, 1991, now U.S. Pat. No. 5,185,667.

TECHNICAL FIELD

This invention relates to the field of imaging systems generally and, more particularly, to the field of surveillance systems. Even more specifically, the present invention relates to a system and method for capturing the individual picture elements of an image, scanning the captured image, transforming at least one selected portion of the image to eliminate a predetermined distortion while magnifying, as appropriate, the selected portion, and outputting the image, either in analog or digital format and without the need for memory buffers. Preferably, the system is implemented in the form of a single integrated circuit incorporating an image sensor array and an application specific integrated circuit coupled thereto.

BACKGROUND ART

Video imaging is touching our lives in increasingly greater ways. For example, video imaging is used for security purposes, tele-conferencing, entertainment, robotics and endoscopic surgery, just to name a few. Video devices monitor and communicate to the masses.

One method of capturing a video image is through a fisheye lens. In such a method, three basic steps are required to yield an intelligible image. Namely, an image is captured using a video camera incorporating the fisheye lens, the image is processed in real-time to remove the optical distortion, and the image, or a portion of interest, is then reconstructed. A method and apparatus for electronically removing distortion from an image captured using a fisheye, wide angle or other lens for receiving a partially spherical image has been described in U.S. Pat. No. 5,185,667 and its progeny including U.S. Pat. Nos. 5,359,363 and 5,313,306 and U.S. application Ser. No. 08/189,585 filed Jan. 31, 1994 and Ser. No. 08/339,663, filed Nov. 14, 1994 all incorporated by reference as to any subject matter contained therein. Using the approach taught therein, the location of the desired output picture element in the input memory buffer is calculated and the input memory is sequenced through as directed by the distortion correcting calculations. One limitation of this approach is that it requires large quantities of fast memory to capture and store the incoming image in sequence so that the calculated addresses can rearrange the image removing the distortion. This method is required due to the standard scan approach used by the vast majority of commercial cameras.

Further, for higher resolution scan conversions, proportionately higher processing frequencies are required, for example, for capturing and digitizing the image, as well as increased capacity of high speed memory. These higher frequency components may be more expensive to implement and operate.

It is well known that conventional digital image arrays are primarily based on two technologies: Charged Coupled Diode (CCD) and Charge Injection Diode (CID) devices. Due to the standardized formats used in various countries—for example, N.T.S.C. is used in the United States and Japan, PAL is used in Europe, S.E.C.A.M. is used in Eastern Europe, the so-called "Grand Alliance" format and European 1250/50 format are suggested presently for high definition television in the United States and Europe respectively and the M.U.S.E. standard presently existent in Japan—for video transmission and reception, the scan sequencing on these arrays is typically top left to bottom right, sequencing through each pixel by row left to right and then by column. In conventional cameras, the captured image impinges on the imaging array in an undistorted manner, the scan thus providing an undistorted image.

For example, with the application of a fisheye lens to the camera, a distorted image impinges on the imaging array and a standardized scan results in a distorted image. The captured image is converted from analog to digital data and stored in a memory buffer. As taught in the Zimmerman '667 patent, the picture elements, or pixels, are scanned in an appropriate nonlinear sequence determined to yield a substantially non-distorted image. The particular pixels and the order in which they are scanned is dependant upon several factors including, for example, the orientation angle (zenith and azimuth angles from the direction of the lens), magnification, and rotation of the image. The transformed image is then converted back from digital to analog and stored in a second memory buffer. The analog data is output, for example, for recording, for display on a video display device or for compression and transmission to a remote location or otherwise utilized.

Charge Injection Diode (CID) imaging systems have been commercially available since the 1970's. CID imaging systems were introduced just prior to the introduction of Charged Coupled Diode (CCD) cameras. Of these competing technologies, the CCD technique has been the more widely used due to its ability to be mass produced and its simplified scanning control method. However, CID's remain in use in special applications due to their radiation tolerance and their ability to integrate light over long periods of time as a result of low light level sensitivity in the visible and infrared spectrums.

It is known that one unique property of CID's relative to CCD's is that they can be directly addressed on a pixel by pixel basis. However, directly addressing each pixel is costly due to the required circuitry needed to generate each address. Other problems that arise in the use of CID technology include interfacing transform hardware to a CID system at the sensor level and increasing the resolution of the CID to support increases in the zooming capability of the hardware.

Recently, new image sensor technology has emerged and has been described, for example, by Eric R. Fossum in his article, "Ultra Low Power Imaging Systems Using CMOS Image Sensor Technology" published in *Proceedings of the S.P.I.E.*, vol. 2267, Advanced Microdevices and Space Science Sensors (1994), incorporated by reference as to any subject matter deemed essential. Therein, a device herein referred to as an active pixel image sensor (APS) is described for manufacture according to complementary metal-oxide-semiconductor (CMOS) fabrication techniques. The APS is integratable with application specific integrated circuits on the same integrated circuit greatly improving access time. The APS image sensor may be provided with on-chip timing, control, signal chain and analog-to-digital conversion (ADC). Of particular importance is that the present device is active, i.e. not a passive device, and with built-in amplification, has improved noise immunity and light pick-up capability. Because of the movement in CMOS technology toward larger and larger capacity random access memories such as dynamic random access memories to 4, 8, 16 and soon 256 megabit capacity, it is entirely conceivable that access time and, just as importantly, resolution are greatly enhanced over either CID or CCD technologies as these devices are fashioned into arrays of greater and greater dimensions.

According to U.S. Pat. No. 5,200,818, issued Apr. 6, 1993, and incorporated herein by reference as to its entire contents, there is disclosed a partially spherical array (FIG. 2) or a circular array (FIG. 3) of CCD sensors which capture an image. It is believed that the captured image will exhibit little inherent distortion since each sensor of each array will capture a small portion of the overall image. The captured image represents the sum of the non-overlapping images captured by the several sensors. In other words, there would be little inherent distortion compared with that of an image captured utilizing a pinhole, fisheye, wide angle lens or other lens which introduces a predetermined distortion. The obvious disadvantage of the '818 patent is the present limited capability to manufacture such an array at reasonable cost.

Therefore, it is an object of this invention to provide a means for directly addressing each picture element of an analog image captured with an imaging device having a field of view, the picture elements being addressed in a non-linear sequence determined in a manner similar to that described by U.S. Pat. No. 5,185,667 to provide a distortion-corrected image without requiring the use of filters and memory holding buffers.

Another object of the present invention is to provide a means for directly addressing each picture element of an analog image captured using an imaging device having a two-dimensional field of view.

Still another object of the present invention is to provide such a means using a CMOS APS, CID or a CCD imaging system and wherein the system may be used for panning, tilting, rotating, and/or magnifying the captured image.

Utilizing a CMOS APS array, a distortion correction engine application specific integrated circuit is mounted on the same semiconductor chip to correct any predetermined distortion introduced by the imaging system array. Moreover, such a device or pair of devices when coupled to a computer controller may comprise the eye or eyes of the information superhighway of the future.

DISCLOSURE OF THE INVENTION

Other objects and advantages will be accomplished by the present invention which is provided for directly scanning, for example, a rectilinear array, partially spherical or circular array or other array of imaging elements using a linear or non-linear scan to eliminate any need for intermediate digital data storage between image capture and image selection and output. Moreover, the method of the present invention is provided for directly addressing each picture element (for high magnification output) or alternate picture elements (for lower magnification output) of an analog image captured with such an imaging device array, having either a partially spherical field of view or a conventional two-dimensional field of view. In the presently preferred case of an imaging device or device array having a partially spherical field of view, picture elements may be addressed in a non-linear sequence, the addresses being determined in a manner similar to that described in U.S. Pat. No. 5,185,667, to provide a distortion-corrected image without requiring the use of distortion correction circuitry, filters or memory holding buffers.

When used with a lens of a conventional camera, the captured image is addressable in a grid fashion, with each pixel center being defined at a crossing point within the grid. With a lens with a partially spherical field of view, the captured image in two-dimensions is circular, thus, contains a predetermined distortion, and is correctable according to the algorithms described by U.S. Pat. No. 5,185,667. An image transform processor is used to appropriately generate picture element addresses depending upon whether the image is supplied via an input for receiving an externally input video signal or internally via a CID, CCD or APS array and upon the particular portion of interest of the image to remove predetermined distortion, if there is significant distortion. In the case of a non-linear scan, the image transform processor is provided with the capability of geometrically filtering the portion of interest of the captured image such that a two-dimensional, undistorted image is output, for example, for recording, for display at a monitor or for transmission. The particular portion of interest of the captured image is dependent, for example, upon the pan, tilt, magnification, and rotation of the captured image, all of which being achievable without moving a lens or sensor array. The particular portion of interest of the captured image is output, for example, for recording, for display on a monitor of a personal computer or on a television receiver or for compression and/or transmission to a remote location.

In the method of the present invention, there are several technologies used in conjunction one with the other. Included are the transformation of an image captured using a lens (if necessary), using a CMOS active pixel image sensor array, or CID or CCD imaging arrays, and Mixed-signal Semiconductor Devices (MSD's). The image transformation approach performs video image correction functions in real-time, converting a predetermined distorted image into a corrected image that can produce multiple views in different directions simultaneously as per U.S. Pat. No. 5,359,363.

A CID camera array, or preferably a CMOS APS array, may be used to capture the image to be scanned. Both types of sensor arrays are directly addressable on a pixel by pixel basis. The use of such arrays in the method of the present invention allows for the elimination of digital memory buffers and other circuitry for generating and storing pixel addresses. The image transform processor of the present invention is preferably an MSD, which is preferably a single cohesive monolithic chip that incorporates imaging, transformation, and output capabilities. One preferred MSD is a mixed signal ASIC device incorporating both analog and digital components. As further described herein, preferably a single semiconductor device according to the present invention will incorporate at least one such sensor array and one such MSD into a single chip, improving memory access time and image resolution. The sensor array may be arranged in such a way as to introduce a predetermined distortion and, yet, permit ease of manufacture, for example, as a flat planar array coupled to a lens in an imaging system. On the other hand, the sensor array may be arranged in such a way as to introduce little or no distortion to the image. In either event, the MSD comounted with the array may be adapted to correct any such introduced predetermined distortion.

BRIEF DESCRIPTION OF THE DRAWINGS

The above mentioned features of the invention will become more clearly understood from the following detailed description of the invention read together with the drawings in which.

DETAILED DESCRIPTION OF THE INVENTION

Figure 2:
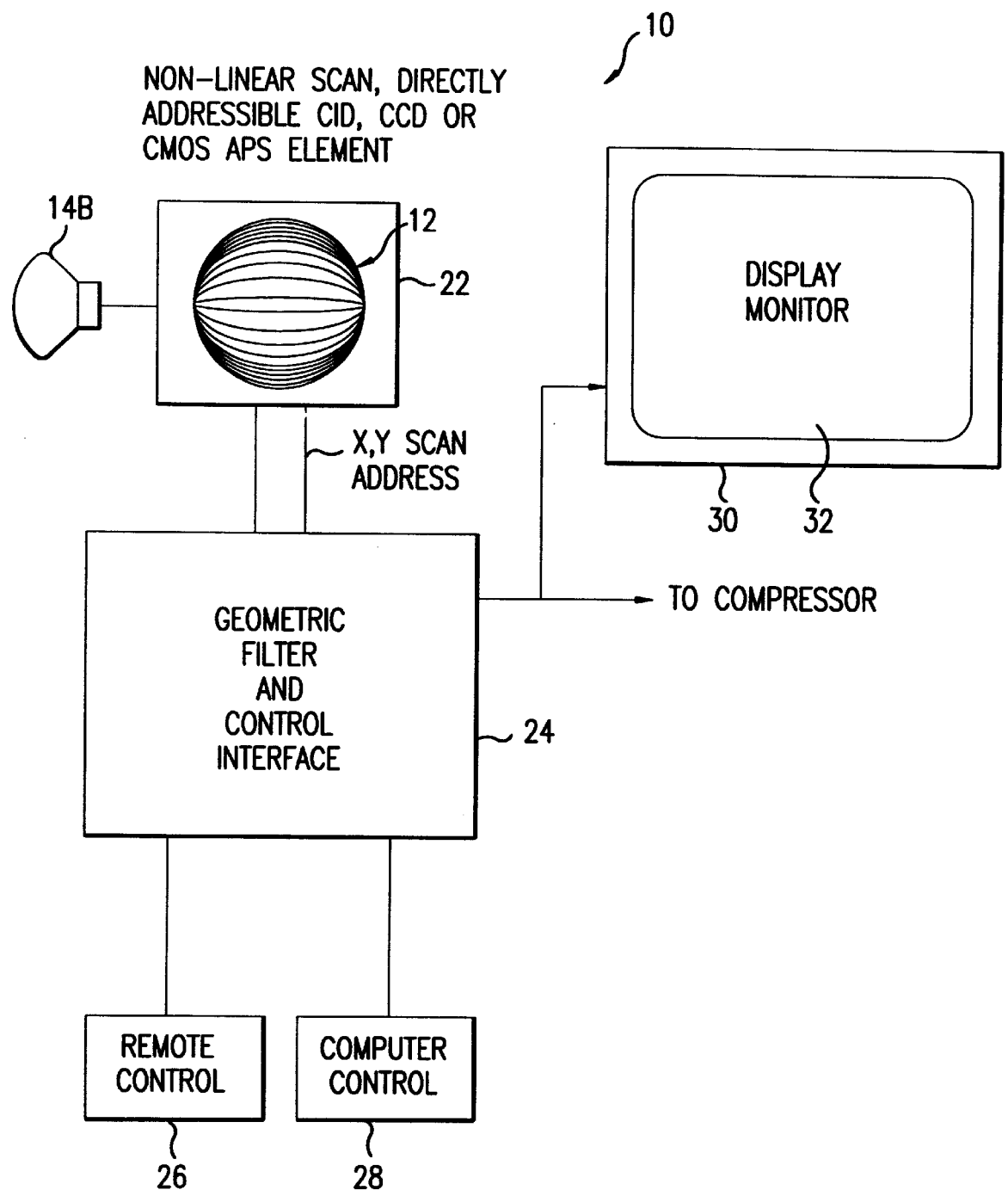
FIG. 2 is a schematic diagram of the method of the present invention for directly scanning a rectilinear imaging element using a non-linear scan wherein one of a non-linear directly addressable charge injection diode or charged coupled diode or, preferably a CMOS APS camera array is used to capture the image.

A method for directly addressing a rectilinear imaging element using either a linear or a non-linear scan is illustrated generally at 10 in the figures. The method for directly scanning a rectilinear imaging element using a non-linear scan, or method 10, of FIG. 2 is provided for directly addressing each picture element of an analog image 12, appearing as a grid, captured with an imaging device or lens 14 having either a partially spherical field of view or a conventional two-dimensional field of view. Referring briefly to FIG. 2, in the method 10 of the present invention, the picture elements 16 of the array 22 are directly addressed in a non-linear sequence determined in a manner similar to that described in U.S. Pat. No. 5,185,667 to provide a distortion-corrected image 12 without requiring the use of distortion correction engines, filters or memory holding buffers. Moreover, in the preferred embodiment the method 10 may incorporate preferably a CMOS active pixel image sensor (APS) array, or either a Charge Injection Diode (CID) or a Charged Coupled Diode (CCD) camera array, or a wide angle, fisheye lens, appropriate coating or conventional focus means coupled thereto or any other conventional imaging system as required. Alternatively, the image sensor array may be fashioned in a manner to collectively capture a relatively distortion free image. In the event a predetermined distortion is introduced by the imaging system, an image processor comprising an MSD may be provided on the same chip, for example, with the sensor array to correct the distortion. The present invention permits panning, tilting, rotating, and magnifying the image 12 captured at array 22 without mechanical movement of the imaging system. Other embodiments for, for example, stereoscopic imaging will be described in connection with the discussion of FIG. 5 and may involve mechanical movement if desired. One preferred sensor array, the CMOS APS sensor array, is described in connection with FIGS. 6–8 and an image processor for correcting any distortion introduced by the sensor array is described in connection with FIG. 9.

Figure 1:
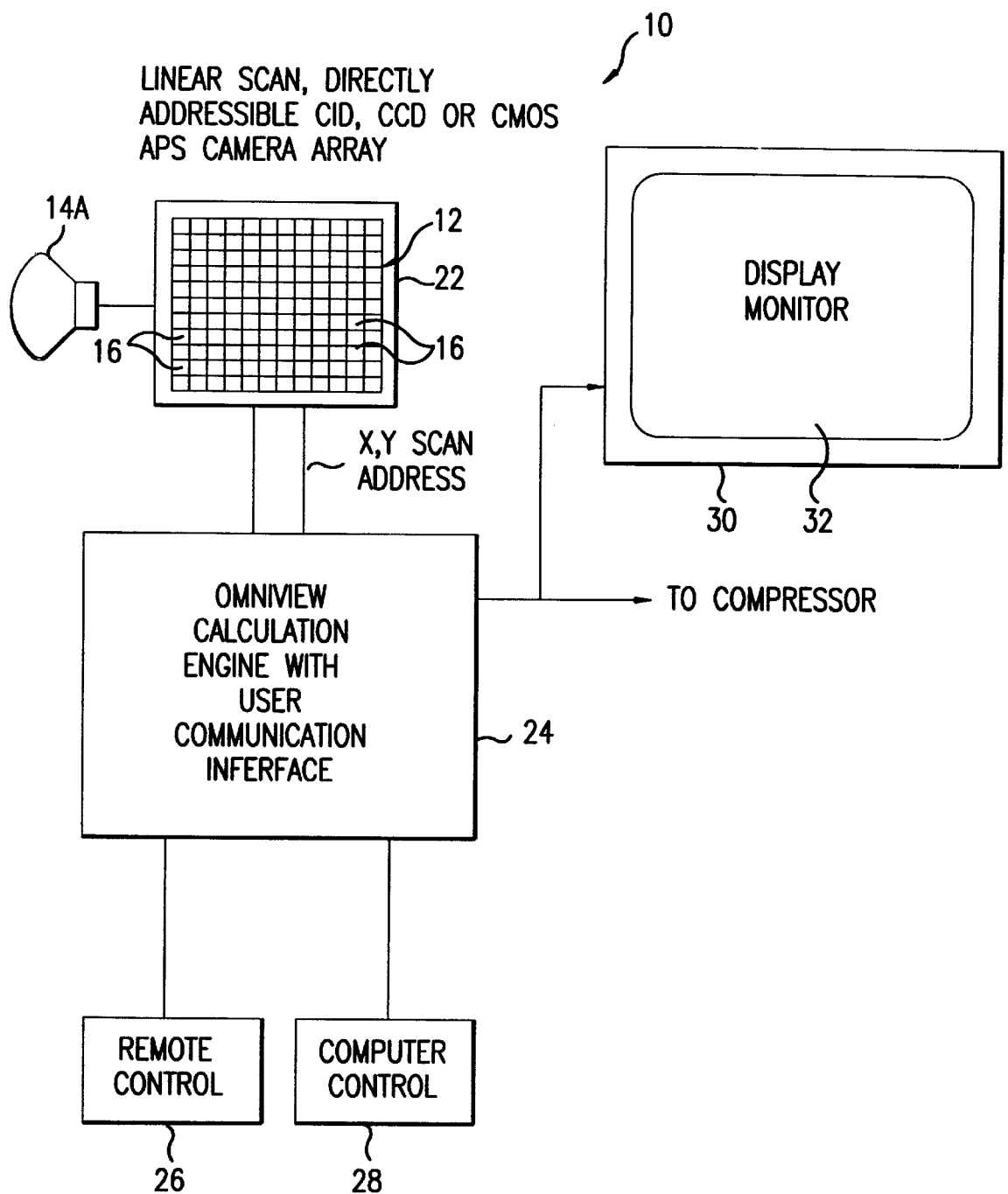
FIG. 1 is a schematic diagram of the method of the present invention for directly scanning a rectilinear imaging element using a linear scan wherein one of a directly addressable charge injection diode, a charged coupled diode, or, preferably a CMOS APS array is used to capture the image.

In FIG. 1, the method 10 of the present invention is schematically illustrated wherein a linear scan is performed and wherein either a directly addressable CMOS APS, CID or a CCD camera array 22 is used to capture the image 12, shown as a grid. The image 12 may be captured through a light focusing apparatus such as the lens 14A of a conventional camera. Together, lens 14A and array 22 comprise an imaging system. An image 12 captured by the camera array 22 is addressable, wherein the address points are defined by a grid. A calculation engine simply comprising simply a geometric filter (for example, a bi-linear digital filter) and control interface or, if predetermined distortion correction is required, an omniview calculation engine with user communication interface 24, is used to process the captured image 12 depending upon the particular portion of interest of the image 12. The particular portion of interest of the captured image 12 is dependent, for example, upon the viewing angle (zenith and azimuth angles), pan, tilt, magnification, and/or rotation of the captured image 12. These particular characteristics are input by a user via a remote control 26 or are preselected via a computer control 28. Computer controller 28 may be any known processor or microprocessor programmed according to the present invention for controlling the engine 24 (or mechanical controllers, not shown). The particular portion of interest of the captured image 12 are output, for example, for display on a monitor 30 or for compression and/or transmission to a remote location (not shown). As will be understood, such images may also be stored on conventional medium such as video tape or may be converted to and stored as digital data. However, conversion to digital data is not necessary to the display of the image, or any portion thereof.

In FIG. 2, the method 10 of the present invention is schematically illustrated wherein, first, a time varying image is captured via the image sensor elements of an array 22. Then, a non-linear scan is periodically performed of the picture elements (pixels) of the array and wherein one of a directly addressable CMOS APS, CID or a CCD sensor array 22 is used to capture the image 12. The lens 14B in this embodiment may be utilized to focus light of an image 12 from a partial spherical field of view. Therefore, the image 12 in two-dimensions as depicted is circular, in particular, spherical (distorted from the grid of image 12 of FIG. 1). In the embodiment of FIG. 2, the image transform processor 24 is provided with the capability of correcting any predetermined distortion introduced by the arrangement of the array 22 and or the lens 14B, that is, the imaging system. Consequently, a selected portion of interest of the captured image 12 selected by remote control 26 may contain a predetermined distortion. For example, a selected image of interest at the upper left of the imaged horizontal lines shown as sphere image 12 contains considerable predetermined distortion. Image processor 24 operates to output a two-dimensional, undistorted image, for example, for display at the monitor 30 or for compression and/or transmission depending on the predetermined distortion introduced by the imaging system. The technology used in the preferred embodiment to correct the distortion of this image 12 is that disclosed in U.S. Pat. No. 5,185,667, incorporated by reference, which describes the omniview calculation algorithms in some detail. Simply put, the non-linear scan of the present invention relates to addressing the stored image data in such a way as to eliminate any distortion.

By linear scanning is intended, in this application, the process of scanning incrementally, for example, one line at a time, pixel by pixel, until an entire image is scanned, and then the process repeats. In accordance with the present invention, particular pixels are addressed in a non-linear sequence in a manner similar to that described by U.S. Pat. No. 5,185,667 to eliminate any predetermined distortions introduced. Thus, looking at an example of reproducing an image portion of the depicted sphere 12 as horizontal lines, a pixel will likely be addressed from the center left of the image rather than the upper left but output in a manner that is consistent with a desired format, i.e. NTSC, PAL, SECAM, or other format, typically, so that it will appear at the upper left or upper center of a displayed image.

Further, in accordance with the present invention and as a consequence of the arrangement of the imaging system 14B, 22, it may be possible to eliminate any distortion, for example, by fashioning the imaging array as a partial sphere or circle as taught by U.S. Pat. No. 5,200,818. However, with present semiconductor fabrication techniques, such an arrangement may be impractical at this time. Nevertheless, any distortion introduced by such an arrangement will be predetermined and correctable according to the principles of the present invention via image processor 24.

For example, if a fish-eye, pinhole, wide angle or related lens is introduced into a system to capture an image of an entire room and adapted to focus its received light on a planar array, a predetermined distortion is introduced into the image which is correctable by non-linear scanning according to the present invention. The imaging system, as will be described herein, contains its own analog-to-digital processors and comprises self-contained erasable memory. Moreover, the imaging system and image processor may be fabricated on a single semiconductor chip. No physical lens may be required as, as discussed herein, the pixels of the array may be coated during fabrication to improve light receptivity or for other reasons. Finally, an image processor is provide on the same chip with the sensor array for eliminating any distortion introduced by the arrangement of the array.

Figure 3:
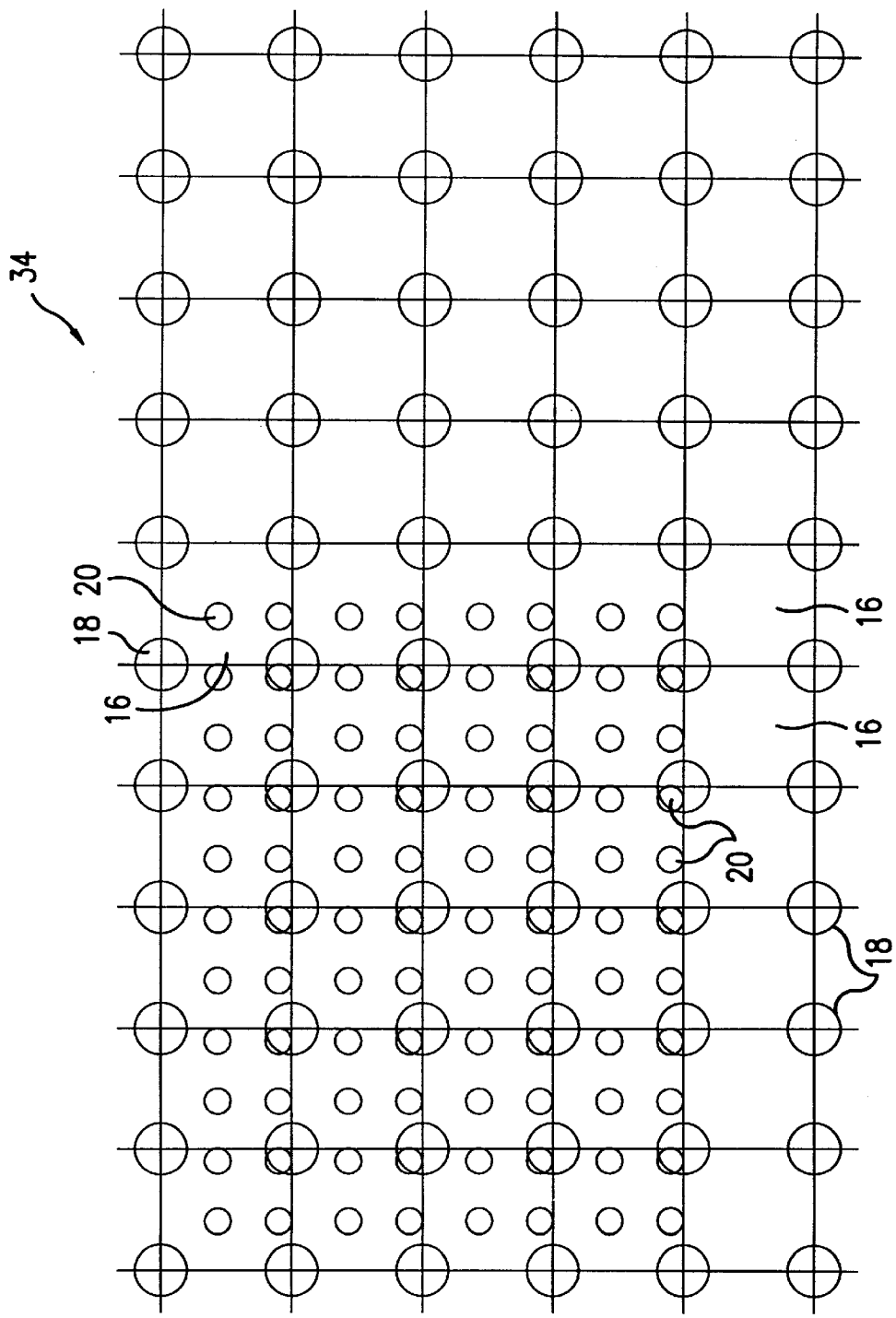
FIG. 3 is a schematic representation of the geometric filtering used in the magnification process associated with the method of the present invention.

Illustrated in FIG. 3 is a schematic representation of the geometric filtering used in the magnification process associated with the method 10 of the present invention. Illustrated is a matrix 34 comprising a number of pixels 16, the center of each being illustrated at 18. In the magnification of the image 12, only a portion thereof, and, thus, a portion of the pixels 16 is selected to fill the image display area 32 of the display device 30. Thus, a plurality of output image pixel centers are calculated as illustrated at 20.

Figure 4:
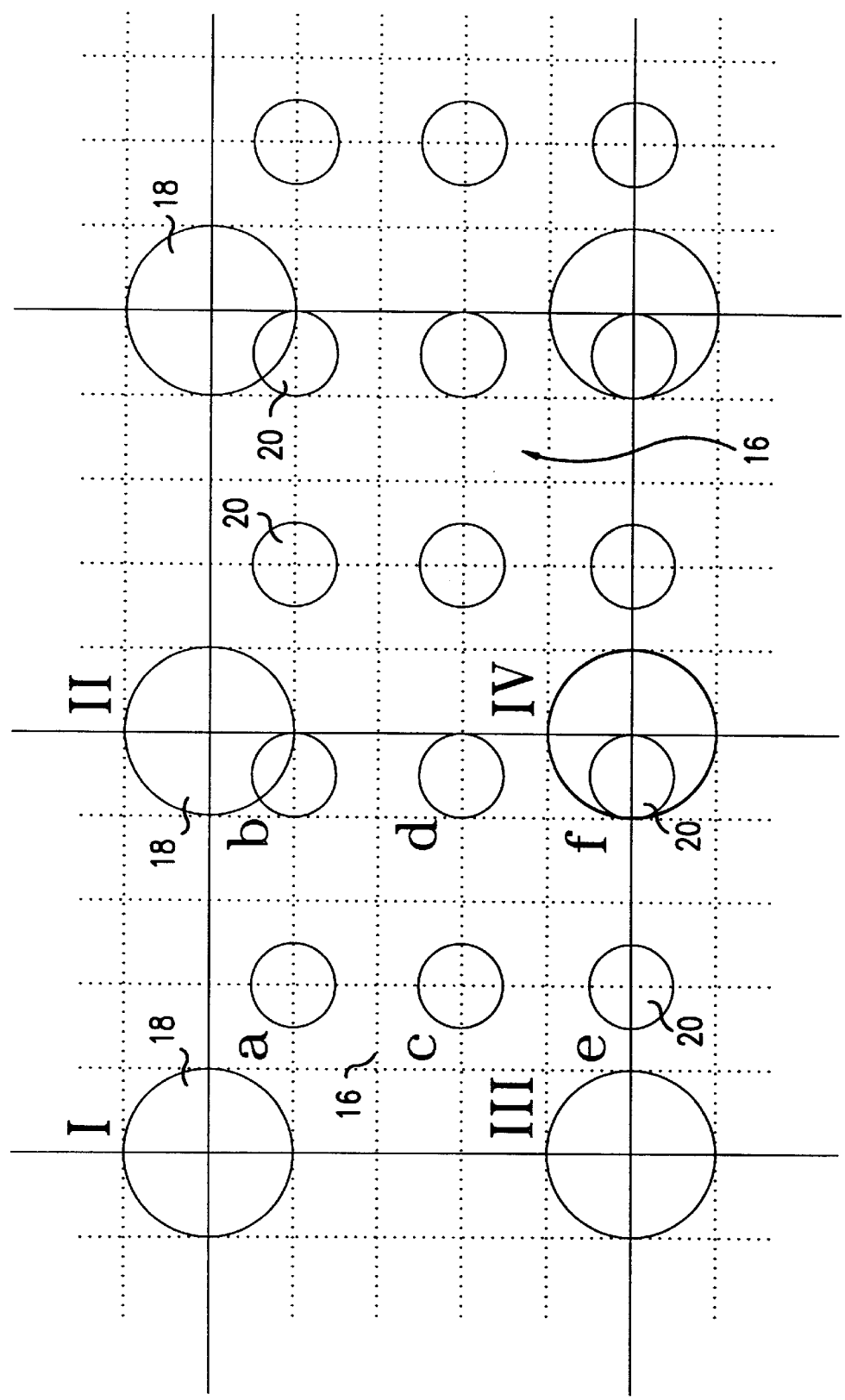
FIG. 4 illustrates an enlarged view of a schematic representation of the geometric filtering used in the magnification process associated with the method of the present invention.

FIG. 4 illustrates a portion of a schematic representation of the geometric filtering used in the magnification process, wherein pixel centers I,II,III and IV are illustrated for purposes of calculating the value of pixel centers a,b,c,d,e and f. Specifically, the values of pixel centers a–f are calculated by the image transform processor 24 based on a weighted average of the values of the pixel centers I–IV as illustrated in the following mathematical expressions:

$a$=(0.6)(0.8)I+(0.4)(0.8)II+(0.6)(0.2)III+(0.4)(0.2)IV

=0.48 I+0.32 II+0.12 III+0.08 IV $b$=(0.1)(0.8)I+(0.9)(0.8)II+(0.1)(0.2)III+(0.9)(0.2)IV

=0.08 I+0.72 II+0.02 III+0.18 IV $c$=(0.6)(0.4)I+(0.4)(0.4)II+(0.6)(0.6)III+(0.4)(0.6)IV

=0.24 I+0.16 II+0.36 III+0.24 IV $d$=(0.1)(0.4)I+(0.9)(0.4)II+(0.1)(0.6)III+(0.9)(0.6)IV

=0.04 I+0.36 II+0.06 III+0.54 IV $e$=(0.6)(0)I+(0.4)(0)II+(0.6)(1)III+(0.4)(1)IV

=0.6 III+0.4 IV $f$=(0.1)(0)I+(0.9)(0)II+(0.1)(1)III+(0.9)(1)IV

=0.1 III+0.9 IV

Other affects may also be accomplished in like manner such as pan and tilt, wherein the desired pixel centers 20 do not correspond with the pixel centers 18 of the captured image 12. In the embodiment wherein a lens 14B with a partially spherical field of view (FIG. 2) is used, the image transform processor 24 is provided for transforming the curvilinear image 12 to an undistorted image such as that illustrated in FIG. 3 in order to perform the functions as described in association with FIG. 4.

In the method of the present invention, there are several technologies used in conjunction one with the other. Namely, the transformation of an image 12 emitting light energy focused using a fish-eye, wide angle, conventional lens or even a coating 14B onto a CMOS APS, CID or CCD image sensor array, and Mixed-signal Semiconductor Devices (MSD's) widely known as application specific integrated circuits (ASIC's). The image transformation method, if required, performs video image correction functions in real-time converting a distorted image according to a predetermined distortion introduced, for example, via the lens or the arrangement of the array, into a corrected image. Moreover, the transformation process can output multiple views in different directions simultaneously. This imaging method 10 precludes the use of mechanical pan and tilt functions of a conventional video surveillance camera.

With respect to CID imaging as compared to CCD imaging, CID's are directly addressable on a pixel by pixel basis. Conventionally, the use of a CID camera array requires the use of costly memory buffers and other circuitry for generating and storing pixel addresses. Memory buffers are typically required to store digital data after such an image has been captured and converted to the digital domain. A second set of memory buffers is also typically required for storing data after having been transformed. However, the image transform processor 24 of the present invention permits the direct addressability of the captured image 12 without necessitating memory buffers on either side of the image transform processor.

Figure 9:
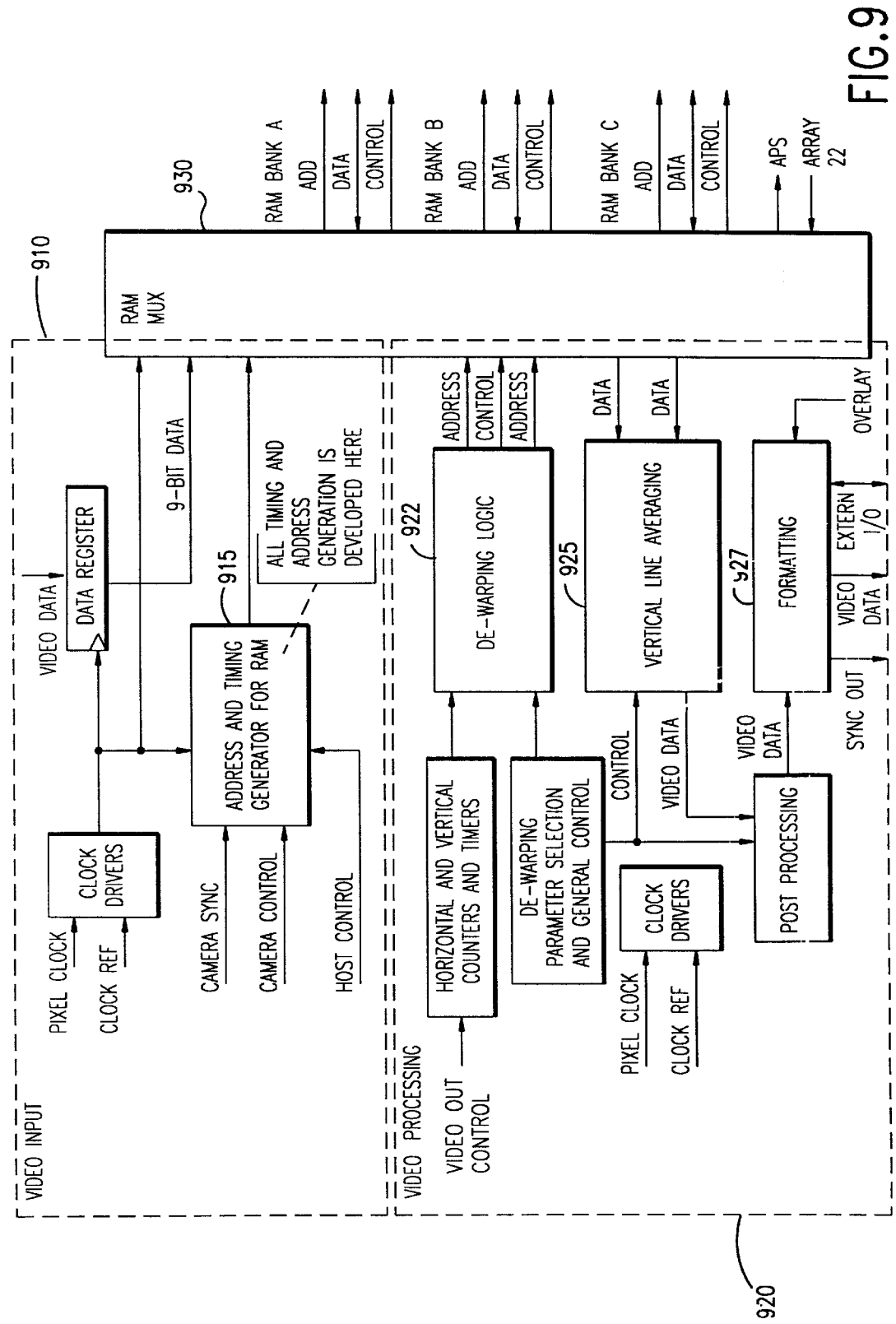
FIG. 9 is a functional block diagram of a converter engine which may be fabricated as an application specific integrated circuit for mounting together with an array of CMOS APS sensors 12 according to FIG. 6 or 7 to correct predetermined distortion in a manner taught by U.S. Pat. No. 5,185,667.

The image transform processor 24 of the present invention, described further in connection with the following discussion of FIGS. 9 is an MSD, which is preferably a single cohesive monolithic chip that incorporates imaging, transformation, and output capabilities. Preferably, the MSD is constructed on the same chip with at least one CMOS APS sensor array to improve access time. One preferred MSD is a mixed signal ASIC device incorporating both analog and digital components.

By incorporating the image transform processor 24 of the present invention with a CMOS APS array or CID array, increased image resolution is provided. Moreover, as per FIG. 2, each element of the array is directly addressable, but only those picture elements are addressed which will provide an image output whereby any predetermined distortion introduced by the imaging system is corrected, for example, via the image transformation processor described by U.S. Pat. No. 5,185,667. Also provided are improvements in unfiltered digital zoom and an image correction that do not require any digital memory if an external video signal input is not provided (see subsequent discussion of FIG. 9). By eliminating the need for digital memory, a sixty percent (60%) cost reduction is accomplished over previous systems. A very high resolution image element can be used (with the advent of, for example, 256 megabit CMOS random access memory technology the conceivable resolution is on the order or thousands of lines by thousands of pixels compared with a conventional 480×640 limitation of current technology), while only selectively scanning a portion thereof to meet the needs of the output display. As a result, at least, a 1024×1024 imaging element can be scanned directly to an NTSC display (480 active lines), if not high definition television applications or high resolution personal computer monitor applications can be met without any frequency conversion or additional transformation.

The use of a CMOS APS or CID camera array as opposed to a CCD array provides several benefits. The CCD element is presently the device of choice for video generation because its cost has been reduced through many generations in the last decade. However, CCD devices are capable only of line scanning. Thus, as the resolution of the CCD device increases, the transmission frequency, the charge transfer efficiency and the switching frequency must increase accordingly, making high resolution CCD systems very expensive. Using a CMOS APS or CID array, the resolution of the sensor can be increased immensely, while the frequency of the scan remains at a constant frequency, as determined by the portion and magnification of the image desired to be displayed at any one instant.

Preferably one such array 22 is mounted on the same semiconductor chip as image processor engine 24. Such a device clearly improves image access time. Utilizing a CMOS APS array 22 improves resolution as well. Moreover, as described in connection with FIG. 2, a non-linear scan is suggested in accordance with the present invention, which eliminates the need for buffer memory and, simultaneously, minimizes the effects of distortion in the output image.

Figure 5:
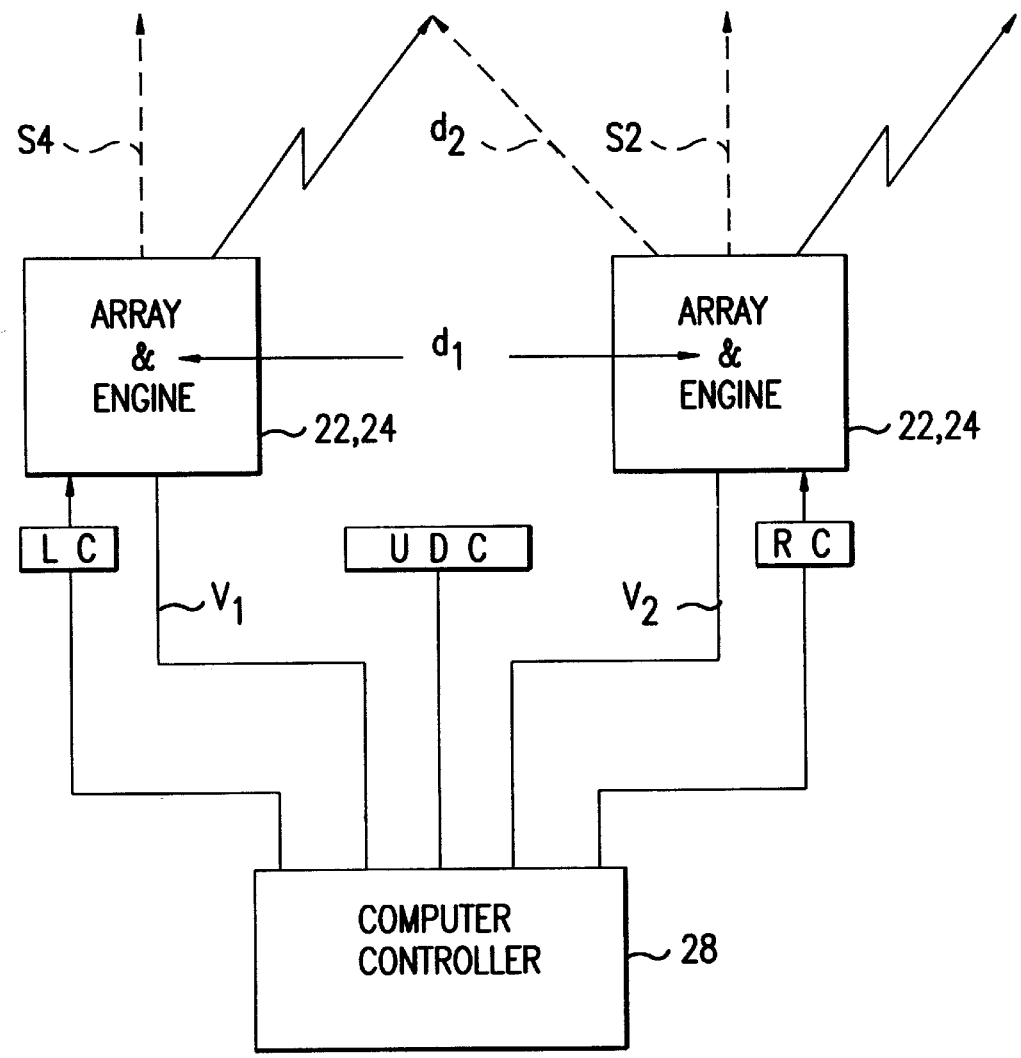
FIG. 5 illustrates an application of a device 12,24 comprising an array and converter engine on the same monolithic chip whereby two are provided having an interdevice distance d1 therebetween under control of computer controller 28 for providing stereoscopic views.

Referring now to FIG. 5, there is shown a particular application of the method and apparatus of FIGS. 1–4 whereby a stereoscopic view may be obtained. The embodiment of FIG. 5 may simulate the eyes 22, 24 of a human-like robot. For example, devices 22, 24 may be separated physically by an interdevice distance d1, for example, simulating the interpupillary distance of human eyes. Computer controller then receives first and second visual output data streams v1 and v2 from the two devices representing two different two dimensional images, respectively. Computer controller 28 thus operates in accordance with a predetermined program to output a stereoscopic, three dimensional, holographic image "seen" via visual outputs v1 and v2 or eyes 22,24.

In such an arrangement, it may be desirable to improve the stereoscopic features of the present invention. A limitation of human eyesight is that an image viewed out of the direct line of sight S will only obtain an effective interpupillary or interdevice distance d2, less than d1, wherein d2 is limited at 0 for an image to the extreme borders (not shown). In other words, d1>d2>0. And at the extreme, effectively, no stereoscopic image is obtained, rather, the same image is viewed by one device further removed from the other device by d1.

This problem may be corrected by providing mechanical controllers for either the left most device or the right most device indicated LC and RC respectively. These may physically move the devices 22,24 so that the desired image is in a direct line of sight and an improved stereoscopic image may again be obtained.

Let us assume that mechanical controllers LC and RC control left, right, up, down movement of the devices as if the devices simulated human eyes. Then, a further mechanical controller may be provided, indicated UDC for simulating the capability of a human neck for moving a human head. Then, according to FIG. 5, the stereoscopic imaging available to a human (or two eyed insect or animal) may be simulated using the present invention.

Now, a concave hemispherical array, (the inverse of the convex array taught by U.S. Pat. No. 5,200,818) may be formed in a sphere with a pin-hole lens to simulate a human eyeball. Such an arrangement, not shown, would provide a substantially undistorted image if utilized in combination with an image processor 24 in accordance with the present invention.

Now the CMOS APS array and engine device 22,24 will be described in further detail wherein FIGS. 6, 7 and 8 describe one such active pixel sensor element of an array of sensors 22 and FIG. 9 describes a functional block schematic diagram of a predetermined distortion correction engine 24.

Figure 6:
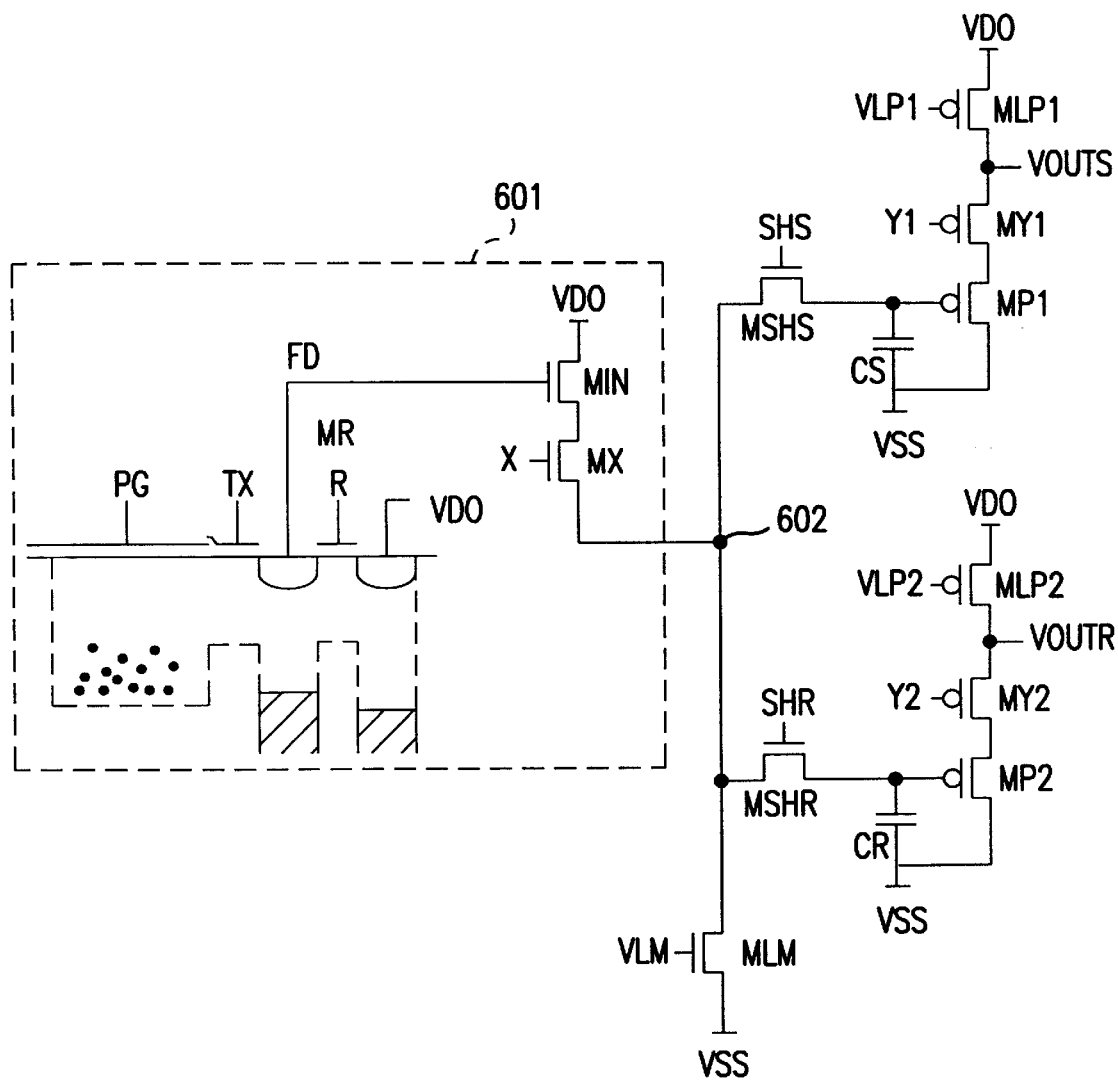
FIG. 6 represents a circuit diagram of the signal chain of a CMOS active pixel image sensor (APS) of the array 12.
Figure 7:
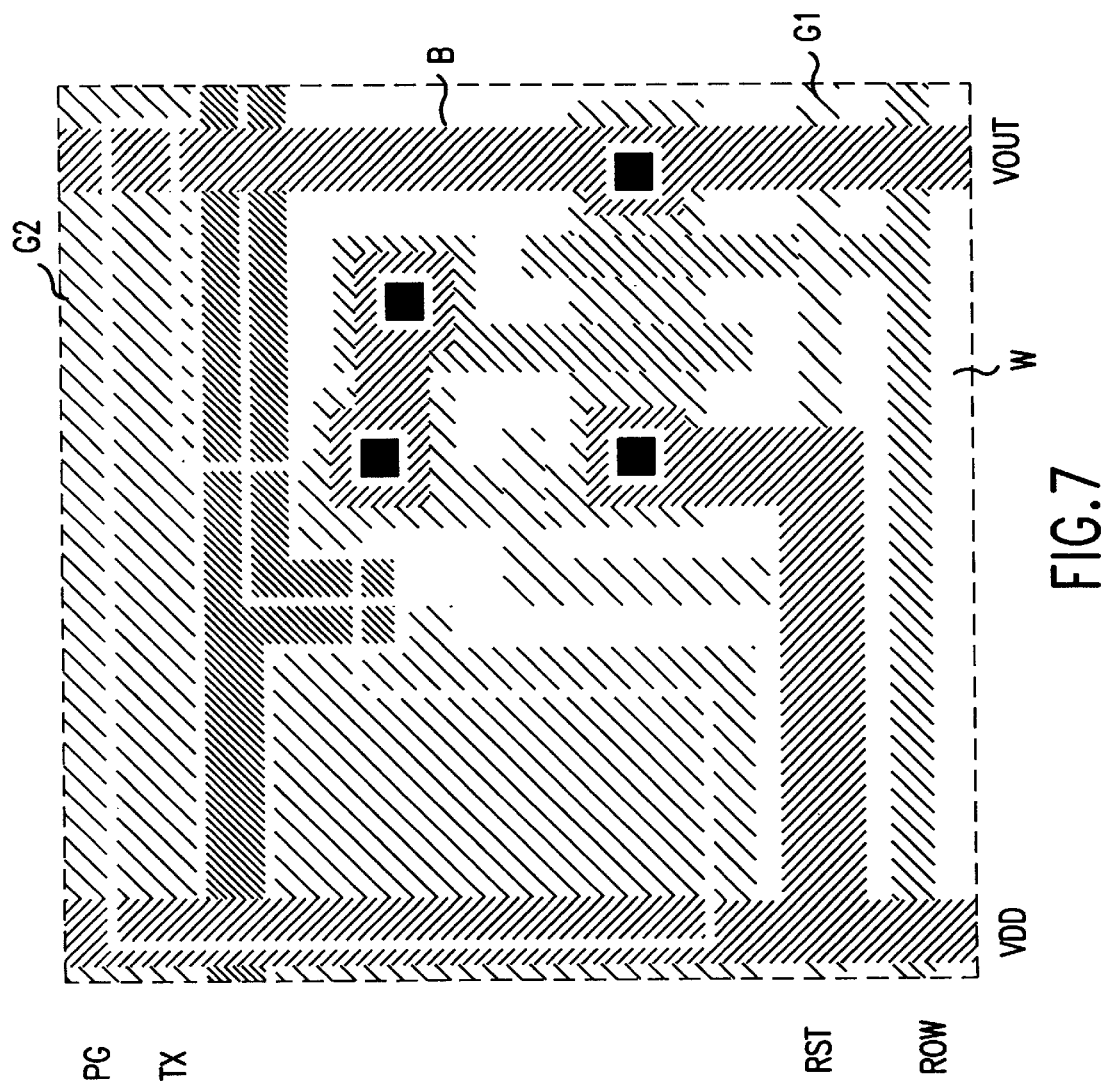
FIG. 7 is a photograph representing a typical semiconductor layout of the CMOS APS photogate pixel corresponding to the APS of FIG. 6.
Figure 8:
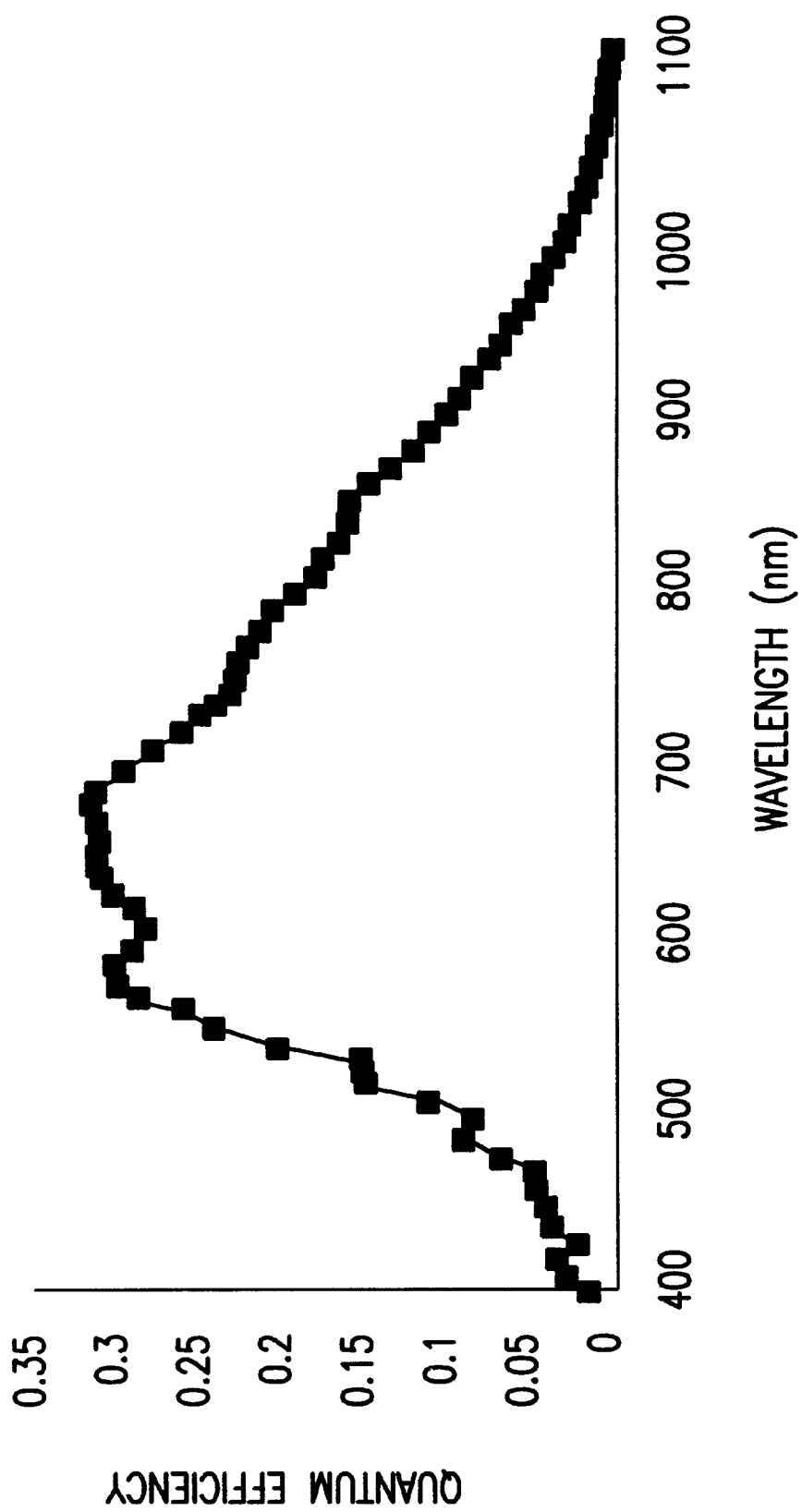
FIG. 8 is a graph of quantum efficiency versus wavelength of light in nanometers for the APS of FIGS. 6 and 7.

FIGS. 6, 7 and 8 describe in some detail a high performance CMOS sensor technology which may be especially suitable for use with a distortion correction engine 24 of the present invention. Each pixel consists of a photoactive region that is an MOS photogate detector, similar to the structure employed in known CCDs. Referring to FIG. 6, the pixel contains a transfer gate 601 (enclosed in dashed lines) and a floating-diffusion source follower output amplifier (hence the name Active Pixel Sensor or APS). The amplifier is also similar to those employed in the output stage of a CCD. Again, the output transistor MLN being within the pixel 601, the pixel is "active" or an active pixel sensor having built-in output amplification. The in-pixel source follower section converts the photogenerated signal output FD of the dashed line section into a voltage at junction 602. The pixel is addressed by a row select switch, and the output of the transistor is fed to a vertical wire running down the column (refer also to FIG. 7). The voltage on this column bus is sensed by an amplifier located at the bottom of each column. The signal is sampled onto a holding capacitor for readout. FIG. 7 comprises a photograph of one typical layout of a CMOS APS photogate pixel which may be deviated from according to the application or exigencies of array building.

Referring again to FIG. 6, the per-column signal chain is shown having two capacitors, Cs and Cr, one Cr for sensing the output of the floating diffusion after reset, and the second Cs for sensing the output following intra-pixel transfer of the signal charge. The two capacitors are buffered by a second source-follower stage that is scanned and selected for readout at Vouts and Voutr respectively. The differential output permits correlated double sampling of the pixel that suppresses kTC noise, 1/f noise, and fixed pattern noise due to threshold voltage offset. Consequently, the present CMOS APS provides a dramatic improvement over previously known CMOS light sensor technology developed in the United Kingdom.

Referring to FIG. 7, the layout is shown in different shades of gray from white W, to gray 1 G1, to gray 2 G2, to black B. For example, TX comprises a horizontal black bar vertically tied to vertical bar VDD. Reset, RST, at first horizontally begins as G1 and extends to the right after approximately the middle of the layout. Moreover, RST extends perpendicularly up from horizontal bar RST and to the right. Gray 2 portions include substantial areas of PG and areas bounded by TX and RST.

Output-referred conversion gain in the CMOS APS depends on the capacitance of the floating diffusion output node. Typical values are 7uV/e(n-well, n-channel). So-called "full-well" of the sensor is determined by the saturation of the signal chain rather than the photogate potential well capacity, and is typically 1.2 V output-referred, or 170,000 electrons for the photogate device. Increasing or decreasing the supply rails results in a change in saturation level of about 0.5 V/V. The photogate potential well capacity is approximately 5,000 e–per square micron per volt, or about 1.5 million electrons for a 20 um pixel with 25% fill factor and 3 V bucket depth.

Other characteristics of one such device are described in Fossum, already incorporated herein by reference.

The pixel can also be implemented using a photodiode detector structure having typical conversion gains of 3uV/e–. The photodiode structure has the advantage of increased blue response by eliminating the polysilicon overlayer, but has a larger capacitance (lower conversion gain, uV/e–) and its kTC noise cannot be suppressed on chip. Thus, signal to noise ratio in the photodiode structure remains nearly constant, though the structure (being a diode in stead of transistor array) is simpler to design and operate. A pinned photodiode structure, as that employed in interline CCDs, can be used to suppress kTC noise but introduces a non-standard CMOS process variation.

The optical fill-factor (percentage of pixel area designed for photodetection) of the APS is approximately the same as an interline CCD (25–30%), and lower than a full frame CCD. On-chip microlenses may be used to boost the effective optical fill-factor to over 60% via an additional backend processing step.

The APS has some of the advantages of a CID for signal collection. Referring to FIG. 8, there is shown an absolute quantum efficiency curve for a CMOS APS implemented with approximately a 25% optical fill factor and no coatings, on-chip microlenses or other enhancement devices or filters. The quantum efficiency is graphed on the vertical axis against wavelength of light along the horizontal axis in nanometers. According to the graph, at either end of the spectrum, improvement may be desired. Improvement in blue/ultraviolet (UV) response can be achieved using phosphors such as lumogen and/or anti-reflection coatings. Improved device design will also boost blue response. As already described, photodiode structures have improved blue response.

In the red to infrared (IR) region of the spectrum, there is reasonable response suitable for, for example, scientific imaging processes and surveillance applications.

The described CMOS APS architecture uses row and column decoders for selecting pixels for readout. Thus, windows-of-interest are implemented as described herein and variable integration periods for different windows can also be achieved, for example, when some spectral bands have weak signals.

Presently, the CMOS APS array is implementable in 1.25 um CMOS technology, however, improvements in CMOS technology anticipate 0.25 um capability within a matter of a few years or less. By incorporating on-chip analog-to-digital conversion into the array, on-chip power dissipation is improved from 7 mW to 5 mW.

Referring to FIG. 1 of the '667 patent, a CMOS APS device according to the present invention may incorporate lens, image sensor and capture, input buffer memory, analog to digital conversion and output amplification, each of which functions apparently performed by separate elements in FIG. 1 and herein, according to the present invention, combined into a single device including an image distortion correction engine ASIC 24 as shown in FIG. 5 and now further described in connection with FIGS. 9. Also, referring to FIG. 9, the external video input (or inputs) 910 and RAM banks A, B and C may be eliminated according to the present invention.

Referring to FIG. 9, there is shown a functional block diagram of a distortion correction engine according to the present invention, hereinafter referred to as a video dewarping engine (VDE). As shown, the VDE is divided into three main sections, a video input section 910, a video processing section 920 and a random access memory multiplexer section, RAM Mux 930.

Referring first to the video input section 910, there is shown video data from an optional, external imaging system (off chip), camera, recorder or the like input to a data register driven by clock drivers, clocked by a pixel clock and a clock reference from a clock and control circuit (not shown). There may be multiple such inputs in accordance with the present invention. The input video data is stored in buffer RAM banks A, B or C for processing.

To implement the non-linear scan embodiment of the present invention as described by FIG. 2, the video data is collected by directly addressing particular pixels determined via the de-warping logic circuit 922 of the video processing section 920 as if the array 22 were coupled as additional RAM, accessible via RAM Mux 930. APS array 22 is directly addressed by video processing section 920 without the need for input buffer memory or RAM banks A, B and C. Regardless of whether the video input is from array 22 or input from externally to the RAM banks, the ASIC depicted in FIG. 9 accepts video data input by whatever means and corrects any predetermined distortion introduced by the imaging system.

In the video input section 910, the clock drivers provide clock drive for address and timing generator 915 for RAM Mux 930 and directly to RAM Mux 930. Address and timing generator 915 also generates timing and addresses for dewarping logic 922. For example, 9-bit resolution video data is input to memory from data registers thereafter via RAM Mux 930. Moreover, the address and timing generator 915 is controlled by control inputs, for example, for selecting an image portion for output as per remote control 26 or computer control 28 (of FIG. 1) here shown as camera sync, camera control and host control leads or data buses. As taught in U.S. Pat. No. 5,185,767, the control input should, at least, provide a viewing angle having zenith and azimuth angle components from a line-of-sight. Other control input data includes rotation, a distortion inherently correctable in accordance with that described system. Moreover, magnification may be input and performed during the distortion correction process. As described herein, alternative or additional magnification can be provided in accordance with FIGS. 3 and 4 during the memory scanning process. Thus, without any need for mechanical movement, a "virtual" camera is panned, tilted, rotated, zoomed or the like in accordance with the present invention.

Referring now to the video output or processing section 920, the selected video data is accessed from RAM banks A,B, or C or from APS array 22 via RAM Mux 930 and operated upon via dewarping logic as required. The dewarping logic 922, in turn, is controlled via horizontal and vertical counters and timers and parameter selection and general control sections respectively. The manipulated data is output to vertical line averaging circuitry 925 and forwarded to post-processing circuits. Vertical line averaging is further described by copending and concurrently filed U.S. patent application Ser. No. 08/373,454. Thereafter, the processed video data is output to formatter circuitry 927. There the data may be selectively overlayed, for example, for teletext messaging or the like and output in a preselected desired format.

The video processing section 920 receives control input as to which of a plurality of formats in which the output may be provided, for example, from NTSC, PAL, SECAM, etc. Moreover, video processing section 920 receives pixel clock and a clock reference in the same manner from a clock and control circuit on board the ASIC (not shown).

From the foregoing description, it will be recognized by those skilled in the art that a method for directly addressably scanning a rectilinear imaging element using a non-linear scan offering advantages over the prior art has been provided. Specifically, the method is provided for directly addressing an image captured using a CCD camera array, a CMOS APS sensor or CID array and outputting a signal for displaying a selected portion of that image in real time without the requirement of digital memory buffers. The elimination of digital memory buffers reduces the hardware costs involved with constructing such a surveillance system by at least sixty percent (60%) as compared to conventional systems. The selected portion of the image is selected through magnification, tilt, pan, and rotation. Such selections are made remotely by a user of the system, or may be pre-selected.

Moreover, a single chip integrated circuit is described which comprises, for example, a picture element sensor array and an application specific integrated circuit together which also eliminates any requirement for buffer memory. Moreover, the circuit may receive a coating during fabrication to improve light energy capture. The array/image processor of the present invention can operate to provide an eye for the so-called information super-highway.

Consequently, applications for the present invention are practically unlimited and may include, for example, inspection during manufacture, monitoring of processes, surveillance applications including security, unsupervised broadcast television, video teleconferencing, target acquisition, endoscopic surgery, robotics, and any other application involving imagery or image reception, processing and transmission.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention:

1. An image processor for directly de-warping data collected using a directly addressable non-linear scan of a rectilinear imaging element comprising:
   an imaging system comprising an array of a plurality of picture element sensors for capturing a light image and
   a digital image transform processor, coupled to the imaging system, comprising a digital application specific integrated circuit for implementing a direct scan of said array and directly addressing selected pixels determined by a de-warping logic circuit of the digital image transform processor to select an image portion, the digital image transform processor eliminating predetermined distortion introduced by the imaging system and outputting a real-time distortion corrected image to vertical line averaging circuitry followed by post-processing circuitry.

2. A semiconductor device as recited in claim 1 wherein each said picture element sensor comprises a CMOS active pixel sensor.

3. A semiconductor device as recited in claim 1 wherein at least one picture element sensor receives a coating to improve light energy receptivity.

4. An imaging system comprising at least two semiconductor devices according to claim 1, the devices being placed a predetermined interdevice distance from one another, each device outputting two dimensional image data, the data being adaptable for conversion to three dimensional data.

5. A method for providing a distortion-free image for use in an image processing system comprising the steps of:
   capturing, by a picture element sensor array, picture elements for a hemispherical/two-dimensional light image; and
   using a digital image transform processor for directly addressing the picture elements in a non-linear sequence determined by a de-warping logic circuit of the digital image transform processor in real-time to eliminate predetermined distortion introduced by the array and sending output data to vertical line averaging circuitry followed by post-processing circuitry.

6. The method for providing a distortion-free image according to claim 5, further including the step of:
   non-linearly scanning said array to eliminate said any distortion from the received image.

7. A processing terminal comprising:
   an imaging system comprising a two-dimensional array of a plurality of picture element sensors for capturing a hemispherical/two-dimensional light image; and
   a digital image transform processor for scanning said array in a non-linear sequence determined by a de-warping logic circuit of the digital image transform processor for selecting an image portion, the digital image transform processor eliminating predetermined distortion introduced by the imaging system and outputting a real-time distortion corrected image and sending output data to vertical line averaging circuitry followed by post-processing circuitry, wherein intermediate storage of data in random access memory after scanning is avoided.

8. A method for geometrically filtering a portion of a captured distorted image to output a selected undistorted portion of the distorted image according to predetermined viewing angles and a magnification, the method comprising the steps of:
   capturing the distorted image;
   receiving the viewing angles and the magnification;
   using a digital image transform processor for converting the predetermined viewing angles and the magnification to a nonlinear sequence of scanning addresses determined by a de-warping logic circuit of the digital image transform processor for the portion of the captured distorted image; and
   scanning the nonlinear sequence of scanning addresses to output the selected undistorted portion in real-time and sending output data to vertical line averaging circuitry followed by post-processing circuitry, wherein intermediate storage of data in random access memory after scanning is avoided.

9. The method of claim 8, wherein the distorted image is distorted by a wide angle lens.

10. The method of claim 8, wherein the distorted image is distorted by a fisheye lens.

11. Apparatus for geometrically filtering a portion of a captured distorted image to output, without storing in memory, a selected undistorted portion of the distorted image according to predetermined viewing angles and a magnification, the apparatus comprising:

an input for receiving the predetermined viewing angles and the magnification;

a digital image transform processor responsive to the input and configured to convert the predetermined viewing angles and the magnification to a nonlinear sequence of scanning addresses determined by a de-warping logic circuit of the digital image transform processor;

an array of picture element sensors coupled to the digital image transform processor and configured to capture the distorted image; and a scanning circuit configured to receive the nonlinear sequence of scanning addresses from the digital image transform processor and to scan the nonlinear sequence of scanning addresses determined by a de-warping logic circuit of the digital image transform processor to output the selected undistorted portion in real-time and send output data to vertical line averaging circuitry followed by post-processing circuitry, wherein intermediate storage of data in random access memory after scanning is avoided.

12. The apparatus of claim 11, further including a camera, the camera including the array.

13. The apparatus of claim 12, wherein the camera includes a wide angle lens in optical communication with the array, the distorted image being distorted by the wide angle lens.

14. The apparatus of claim 12, wherein the camera includes a fisheye lens in optical communication with the array, the distorted image being distorted by the fisheye lens.

15. The apparatus of claim 12, wherein the image processor comprises a geometric filter.

16. The apparatus of claim 11, wherein each of the picture elements sensors comprises a CMOS active pixel sensor.

17. An image processing device for directly de-warping data collected by a plurality of image sensors using a directly addressable non-linear scan of a rectilinear imaging element comprising:

the plurality of the image sensors, arranged to capture a light image to provide an array of data;

a converter engine having a video input unit for providing camera synchronization, camera control and host control and timing and address generation and a video processing unit with a digital image transform processor, where the video input unit and the video processing unit are coupled to a random access memory multiplexer which receives the array from the image sensors, where the video processing unit includes a digital application specific integrated circuit for implementing a direct scan of said array by directly addressing selected pixels determined by a de-warping logic circuit of the digital image transform processor to select an image portion and use vertical line averaging circuitry to eliminate distortion of the light image and output a real-time distortion corrected image.

* * * * *